US012623089B2

(12) United States Patent
Wang

(10) Patent No.: US 12,623,089 B2
(45) Date of Patent: May 12, 2026

(54) RADIOTHERAPY DEVICE AND MICROWAVE SOURCE THEREOF

(71) Applicant: SHANGHAI UNITED IMAGING HEALTHCARE CO., LTD., Shanghai (CN)

(72) Inventor: Peng Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 988 days.

(21) Appl. No.: 17/808,299

(22) Filed: Jun. 22, 2022

(65) Prior Publication Data

US 2022/0314018 A1 Oct. 6, 2022

Related U.S. Application Data

(63) Continuation of application No. PCT/CN2019/127480, filed on Dec. 23, 2019.

(51) Int. Cl.
| | |
|---|---|
| *A61N 5/02* | (2006.01) |
| *A61N 5/04* | (2006.01) |
| *H01J 23/04* | (2006.01) |
| *H01J 23/05* | (2006.01) |
| *H01J 25/50* | (2006.01) |

(52) U.S. Cl.
CPC .............. *A61N 5/022* (2013.01); *A61N 5/04* (2013.01); *H01J 23/05* (2013.01)

(58) Field of Classification Search
CPC ........... A61N 5/022; H01J 23/04; H01J 25/50
See application file for complete search history.

(56) References Cited

U.S. PATENT DOCUMENTS

| | | | |
|---|---|---|---|
| 2,617,967 | A | 11/1952 | Fisher |
| 2,930,933 | A | 3/1960 | Griffin, Jr. et al. |

(Continued)

FOREIGN PATENT DOCUMENTS

| | | |
|---|---|---|
| CN | 1034823 A | 8/1989 |
| CN | 103839739 A | 6/2014 |

(Continued)

OTHER PUBLICATIONS

International Search Report in PCT/CN2019/127480 mailed on May 6, 2020, 4 pages.

(Continued)

*Primary Examiner* — Joseph L Williams
(74) *Attorney, Agent, or Firm* — METIS IP LLC

(57) ABSTRACT

A microwave source used in the radiotherapy device can be provided. The microwave source may include an anode block and one or more cathodes. The cathode of the microwave source may include a cathode support element having a plurality of slots. The plurality of slots can be axially around a circumference of the cathode support element. The microwave source may include a cathode heater including at least one filament. A first part of the at least one filament may be wound around the cathode support element along a first direction and received by a first portion of the plurality of slots, and a second part of the at least one filament may be wound around the cathode support element along a second direction and received by a second portion of the plurality of slots.

20 Claims, 9 Drawing Sheets

<u>320</u>

(56) References Cited

U.S. PATENT DOCUMENTS

| | | | |
|---|---|---|---|
| 3,255,375 A | 6/1966 | Ward | |
| 3,297,901 A * | 1/1967 | Macdonald | H01J 23/05 |
| | | | 313/340 |
| 4,011,481 A * | 3/1977 | Preist | H01J 21/10 |
| | | | 313/302 |
| 5,350,969 A | 9/1994 | Gattuso | |
| 2004/0187539 A1 | 9/2004 | Ishizuka et al. | |
| 2005/0029917 A1 | 2/2005 | Aiga et al. | |
| 2014/0035435 A1 | 2/2014 | Weber | |
| 2014/0205073 A1 | 7/2014 | Tkaczyk et al. | |
| 2018/0211809 A1 | 7/2018 | Burke et al. | |
| 2018/0350550 A1 | 12/2018 | Terletska et al. | |

FOREIGN PATENT DOCUMENTS

| | | | |
|---|---|---|---|
| CN | 105414732 A | 3/2016 | |
| CN | 105869972 A | 8/2016 | |
| CN | 106816350 A | 6/2017 | |
| CN | 107432992 A | 12/2017 | |
| CN | 109585237 A | 4/2019 | |
| CN | 111729212 A | 10/2020 | |
| EP | 2589412 A1 | 5/2013 | |
| JP | H02086026 A | 3/1990 | |
| JP | H02117051 A | 5/1990 | |
| JP | 2006100066 A | 4/2006 | |
| WO | 2011058361 A1 | 5/2011 | |

OTHER PUBLICATIONS

Written Opinion in PCT/CN2019/127480 mailed on May 6, 2020, 5 pages.

The Extended European Search Report in European Application No. 19957203.3 mailed on Nov. 7, 2022, 8 pages.

Result of consultation in European Application No. 19957203.3 mailed on Nov. 20, 2024, 4 pages.

The Extended European Search Report in European Application No. 25170338.5 mailed on Jul. 8, 2025, 7 pages.

International Search Report in PCT/CN2021/087063 mailed on Jul. 1, 2021, 4 pages.

Written Opinion in PCT/CN2021/087063 mailed on Jul. 1, 2021, 5 pages.

* cited by examiner

200

320

RADIOTHERAPY DEVICE AND MICROWAVE SOURCE THEREOF

CROSS-REFERENCE TO RELATED APPLICATIONS

This application is a continuation of International Application No. PCT/CN2019/127480, filed on Dec. 23, 2019, the content of which is hereby incorporated by reference.

TECHNICAL FIELD

This disclosure generally relates to a radiotherapy device, and more particularly, to a microwave source used in the radiotherapy device.

BACKGROUND

Radiation therapy is widely used in cancer treatment and is also beneficial to several other health conditions. A radiotherapy device (e.g., a linear accelerator) is often utilized to perform the radiation therapy. In the radiotherapy device, a microwave source, composed of an anode and a cathode, is configured to produce microwave pulses (or radio frequency pulses) for controlling the generation of radiation beams (e.g., X-rays). The microwave source is an important component for the radiotherapy device. In some cases, the cathode of the microwave source breaks easily due to frequent deformation of the cathode heater, and such malfunction often affects the normal use of the radiotherapy device. Therefore, it is desirable to develop a high-quality microwave source used in the radiotherapy device.

SUMMARY

In a first aspect of the present disclosure, a cathode of a microwave source may be provided. The cathode may include a cathode support element having a plurality of slots and a cathode heater including at least one filament. The plurality of slots may be axially around a circumference of the cathode support element. A first part of the at least one filament may be wound around the cathode support element along a first direction and received by a first portion of the plurality of slots, and a second part of the at least one filament may be wound around the cathode support element along a second direction and received by a second portion of the plurality of slots.

In some embodiments, the first part of the at least one filament and the second part of the at least one filament may be substantially parallel, and when the at least one filament is powered by a power source, directions of respective current flows of the first part and the second part of the at least one filament may be inversed.

In some embodiments, the first portion of the plurality of slots and the second portion of the plurality of slots may be spaced axially around the circumference of the cathode support element.

In some embodiments, a depth of a slot of the plurality of slots may be greater than or equal to a diameter of one of the at least one filament, and a width of the slot may be greater than or equal to the diameter of the filament.

In some embodiments, the diameter of the filament may be in a range of 0.4 mm to 0.8 mm.

In some embodiments, the at least one filament may be made of a high-melting-point and conductive material.

In some embodiments, the at least one filament may include at least one of tungsten, molybdenum, rhenium, or iridium.

In some embodiments, the cathode support element may be made of an insulative material.

In some embodiments, the cathode support element may include at least one of plastic, rubber, glass, ceramic.

In some embodiments, the cathode may include a thermionic emitter configured to release electrons when the thermionic emitter is heated by the cathode heater.

In a second aspect of the present disclosure, a microwave source may be provided. The microwave source may include an anode block and a cathode centered in the anode block. In some embodiments, the cathode may include may include a cathode support element having a plurality of slots and a cathode heater including at least one filament. The plurality of slots may be axially around a circumference of the cathode support element. A first part of the at least one filament may be wound around the cathode support element along a first direction and received by a first portion of the plurality of slots, and a second part of the at least one filament may be wound around the cathode support element along a second direction and received by a second portion of the plurality of slots. In some embodiments, the first part of the at least one filament and the second part of the at least one filament may be substantially parallel, and when the at least one filament is powered by a power source, directions of respective current flows of the first part and the second part of the at least one filament may be inversed.

In a third aspect of the present disclosure, a radiotherapy device can be provided. The radiotherapy device may include a linear accelerator. The linear accelerator may include an electron generator configured to emit electrons along a beam path, a microwave source configured to generate microwaves and an accelerator tube configured to accelerate the electrons emitted by the electron generator in response to the microwaves. The microwave source may include an anode block and a cathode centered in the anode block. The cathode may include may include a cathode support element having a plurality of slots and a cathode heater including at least one filament. The plurality of slots may be axially around a circumference of the cathode support element. A first part of the at least one filament may be wound around the cathode support element along a first direction and received by a first portion of the plurality of slots, and a second part of the at least one filament may be wound around the cathode support element along a second direction and received by a second portion of the plurality of slots.

In some embodiments, the first part of the at least one filament and the second part of the at least one filament may be substantially parallel, and when the at least one filament is powered by a power source, directions of respective current flows of the first part and the second part of the at least one filament may be inversed.

In a fourth aspect of the present disclosure, a microwave source can be provided. The microwave source may include an anode block and multiple cathodes. When an individual cathode of the multiple cathodes is removably positioned in a center of the anode block, microwaves having a specific frequency may be generated in response to an occurrence of a resonance effect caused by the anode block and the cathode.

In some embodiments, diameters of at least two of the multiple cathodes may be different.

In a fifth aspect of the present disclosure, a radiotherapy device can be provided. The radiotherapy device may include a linear accelerator. The linear accelerator may include an electron generator configured to emit electrons along a beam path and a microwave source configured to generate microwaves. The microwave source may include an anode block and multiple cathodes. When an individual cathode of the multiple cathodes is removably positioned in a center of the anode block, microwaves having a specific frequency may be generated in response to an occurrence of a resonance effect caused by the anode block and the cathode.

In some embodiments, the radiotherapy device may include an accelerator tube configured to accelerate the electrons emitted by the electron generator in response to the microwaves having the specific frequency.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
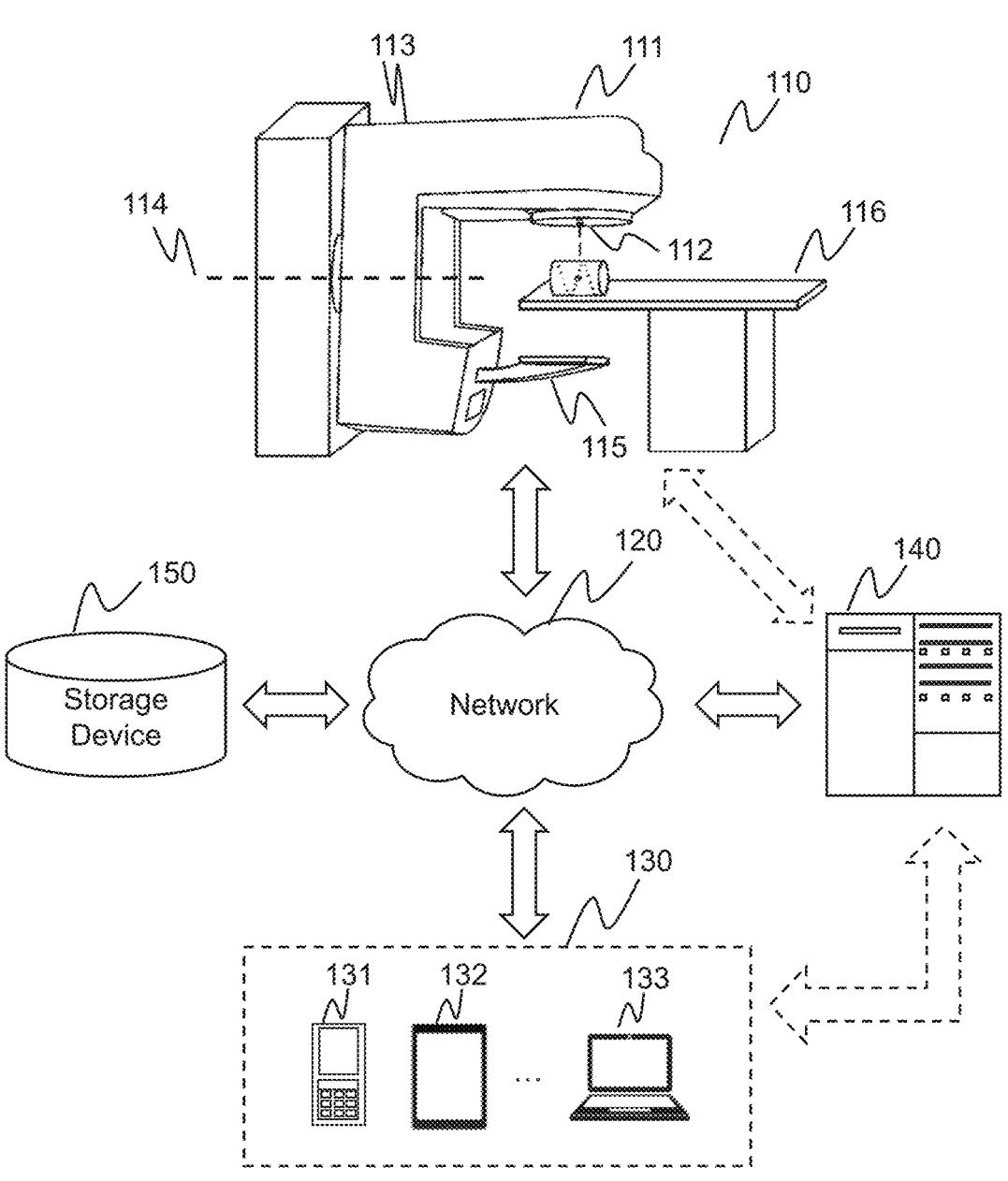
FIG. 1 is a schematic diagram illustrating an exemplary radiotherapy system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The following description is provided with reference to exemplary embodiments that a medical device includes a microwave source (e.g., a magnetron) unless otherwise stated. However, it is understood that it is for illustration purposes only and not intended to limit the scope of the present disclosure. The microwave source disclosed herein may be suitable for other applications (e.g., a microwave oven, a particle accelerator, etc.). Merely by way of example, the medical device may include a radiotherapy device, such as an image-guided radiotherapy (IGRT) device. The IGRT device may include an imaging component (e.g., MRI device, PET device, or CT device) and a radiation therapy component (e.g., a linear accelerator).

Various embodiments provided herein with reference to a microwave source composed of an anode block and one or more cathodes. In some embodiments, the microwave source (e.g., a single-cathode microwave source) may include an anode block and a cathode centered in the anode block. In some embodiments, the microwave source (e.g., a multi-cathode microwave source) may include an anode block and multiple cathodes. The multiple cathodes may share the same anode block. In some embodiments, one of the multiple cathodes can be removably positioned in the center of the anode block. Diameters of the multiple cathodes may be different. In response to an occurrence of a resonance effect caused by the anode block and the cathode, microwaves having a specific frequency may be generated. For example, when a first cathode is positioned in the anode block, first microwaves having a first frequency may be generated due to the resonant effect caused by the anode block and the first cathode. As another example, when a second cathode is positioned in the anode block, second microwaves having a second frequency may be generated due to the resonant effect caused by the anode block and the second cathode. The first frequency and the second frequency may be different. Different microwave powers can be output. Compared with the single-cathode microwave source, the multi-cathode microwave source may output alternative microwave powers and/or frequencies by grouping the anode block and a cathode of the multiple cathodes.

In some embodiments, the microwave source may include a specific cathode design in order to prolong a service life of the cathode. For example, a cathode heater may include at least one filament in a double helix configuration (e.g., double helix filament). The at least one filament can be received by a plurality of slots disposed on a cathode support element. A first part of the at least one filament and A second part of the at least one filament may be substantially parallel. When the at least one filament is powered by a power source, directions of respective current flows of the first part and the second part of the at least one filament are inversed, which may reduce the deformation of the filament caused by an attractive force between adjacent coiled segments of a conventional single helix filament. Besides, the use of the slots may facilitate to fix the filament in order to reduce the deformation of the filament. The service life of the filament may be prolonged to some extent.

FIG. 1 is a schematic diagram illustrating an exemplary radiotherapy system according to some embodiments of the present disclosure. As shown in FIG. 1, radiotherapy system 100 may include a radiotherapy device 110, a network 120, one or more terminals 130, a processing device 140, and a storage device 150.

The radiotherapy device 110 may deliver a radiation beam to a target object (e.g., a patient, or a phantom). In some embodiments, the radiotherapy device 110 may include a linear accelerator (also referred to as "linac") 111. The linac 111 may generate and emit a radiation beam (e.g., an X-ray beam) from a treatment head 112. The radiation beam may go through one or more collimators (e.g., a primary collimator and/or a multi-leaf collimator (MLC)) of certain shapes, and enter into the target object. In some embodiments, the radiation beam may include electrons, photons, or other types of radiation. In some embodiments, the energy of the radiation beam may be in the megavoltage range (e.g., >1 MeV), and may therefore be referred to as megavoltage beam. The treatment head 111 may be coupled to a gantry 113. The gantry 113 may rotate, for example, clockwise or counter-clockwise around a gantry rotation axis 114. The treatment head 112 may rotate along with the gantry 113. In some embodiments, the radiotherapy device 110 may include an imaging element 115. The imaging element 115 may receive the radiation beam that passes through the target object, and generate images of patients and/or phantoms before, during and/or after a radiation treatment or a correction process based on received radiation beam. The imaging element 115 may include an analog detector, a digital detector, or the like, or a combination thereof. The imaging element 115 may be connected to the gantry 113 in any connection means, including an extendible housing. Thus, the rotation of the gantry 113 may cause the treatment head 112 and the imaging element 115 to rotate in a coordinated manner. In some embodiments, the radiotherapy device 110 may also include a table 116. The table 116 may support a patient during a radiation treatment or imaging, and/or support a phantom during a correction process of the radiotherapy device 110. The table 116 may be adjustable to suit for different application scenarios.

The network 120 may include any suitable network that can facilitate exchange of information and/or data for the radiotherapy system 100. In some embodiments, one or more components of the radiotherapy system 100 (e.g., the radiotherapy device 110, the terminal 130, the processing device 140, the storage 150, etc.) may communicate information and/or data with one or more other components of the radiotherapy system 100 via the network 120. For example, the processing device 140 may obtain plan data from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiotherapy system 100 may be connected to the network 120 to exchange data and/or information.

The terminal(s) 130 may enable interactions between a user and the radiotherapy system 100. The terminal(s) 130 may include a mobile device 131, a tablet computer 132, a laptop computer 133, or the like, or any combination thereof. In some embodiments, the mobile device 131 may include a smart home device, a wearable device, a mobile terminal, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile terminal may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the radiotherapy device 110, the terminal(s) 130, and/or the storage device 150. In some embodiments, the processing device 140 may perform one or more radiotherapy operations. For example, the processing device 140 may process plan data (e.g., from a treatment planning system (TPS)), and determine motion parameters that may be used to control the motions of multiple components in the radiotherapy device 110. In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the radiotherapy device 110, the terminal 130, and/or the storage device 150 via the network 120. As another example, the processing device 140 may be directly connected to the radiotherapy device 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiotherapy system 100 (e.g., the processing device 140, the terminal 130, etc.). One or more components in the radiotherapy system 100 may access the data or instructions stored in the storage device 150 via the network 120. In some embodiments, the storage device 150 may be directly connected to or communicate with one or more other components in the radiotherapy system 100 (e.g., the processing device 140, the terminal 130, etc.). In some embodiments, the storage device 150 may be part of the processing device 140. In some embodiments, the processing device 140 may be connected to or communicate with the radiotherapy device 110 via the network 120, or at the backend of the processing device 140.

Figure 2:
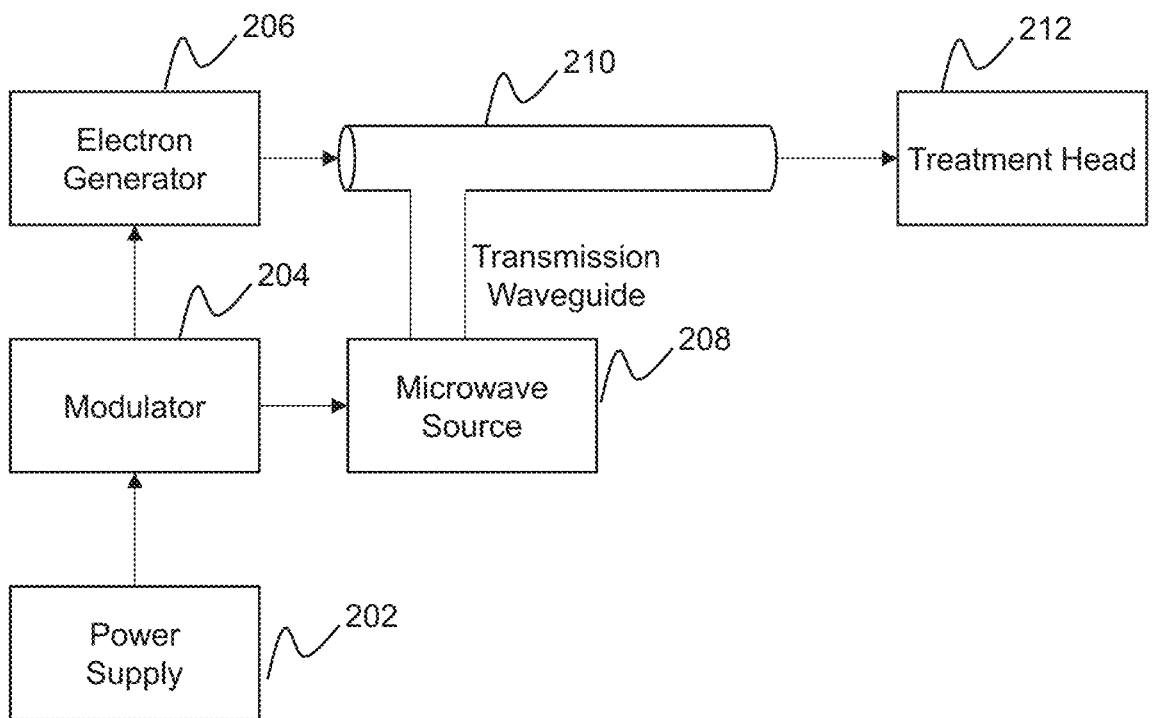
FIG. 2 is a schematic diagram illustrating exemplary components of a linear accelerator according to some embodiments of the present disclosure.

FIG. 2 is a schematic diagram illustrating exemplary components of a linear accelerator (linac) according to some embodiments of the present disclosure. In some embodiments, linac 200 illustrated in FIG. 2 may be implemented on a radiotherapy device (e.g., the radiotherapy device 110). As illustrated in FIG. 2, the linac 200 may include a power supply 202, a modulator 204, an electron generator 206, a microwave source 208, an accelerator tube 210 and a treatment head 212. In some embodiments, the power supply 202 may be configured to provide high voltages (e.g., 45 kV) required for proper modulator operation. In some embodiments, the power supply 202 may include an alternating current (AC) circuit for supplying the alternating current voltage (ACV). In some embodiments, the power supply 202 may include a direct-current (DC) circuit for supplying the direct current voltage (DCV). The modulator 204 may be configured to simultaneously provide high voltage pulses (e.g., DC pulses) to the electron generator 206 and the microwave source 208. The electron generator 206 (e.g., an electron gun, or an electron emitter) may produce electrons injected into the accelerator tube 210. For example, the electron generator 206 may produce electrons along a range of angles and emit the electrons along a beam path. The electron beam may be injected into the accelerator tube 210. The electrons in the accelerator tube 210 may be accelerated at one or more ranges of kinetic energy using microwaves at one or more ranges of frequency. The accelerated electrons may be transmitted to the treatment head 212 for generating a radiation beam. For example, the accelerated electrons may strike a target (e.g., an X-ray target) to generate the radiation beam (e.g., X-ray beam). The radiation beam may go through one or more collimators (e.g., a primary collimator and/or a multi-leaf collimator (MLC)) of certain shapes to form a collimated radiation beam. The collimated radiation beam may irradiate a target object (e.g., a lesion of a subject) to implement radiotherapy.

In some embodiments, the microwave source 208 may be configured to generate the microwaves at one or more ranges of frequency. The microwave source 208 may be deemed as an oscillator that transforms the DC pulses from the modulator 204 into microwave pulses. In some embodiments, the microwave source 208 may be a magnetron or a klystron. In some embodiments, the microwave source 208 may include a magnetron (also referred to as single-cathode magnetron) composed of one cathode and one anode block. In some embodiments, the microwave source 208 may include a magnetron (also referred to as multi-cathode magnetron) composed of multiple cathodes and one anode block. The multiple cathodes may share the same anode block. Through different arrangements of the cathode and the anode block, the microwave sources 208 may output different microwave powers.

In some embodiments, the microwave source 208 may be a magnetron. In the magnetron, the cathode may be heated by a cathode heater. The cathode heater may include at least one filament. The electrons released from the cathode may be accelerated toward the anode block by the action of pulsed DC electric field. The anode block may include a plurality of resonant cavities. In some embodiments, at least one electromagnet may be disposed surrounding the anode block. A static magnetic field may be applied perpendicular to a cross-section plane of the plurality of resonant cavities. The released electrons can move in complex spirals toward the resonant cavities due to influence of the magnetic field. A resonance effect (or the resonance phenomenon) may occur when the resonant cavities begin to resonate at a certain resonance frequency (e.g., 3000 MHz). Thus, the resonant cavities may emit microwaves. The microwaves may be transmitted to the accelerator tube 210 through a transmission waveguide. The electrons in the accelerator tube 210 may be accelerated by the microwave power. More descriptions regarding components of the microwave source may be found elsewhere in the present disclosure (e.g., FIGS. 3A-9, and the descriptions thereof).

Figure 3A:
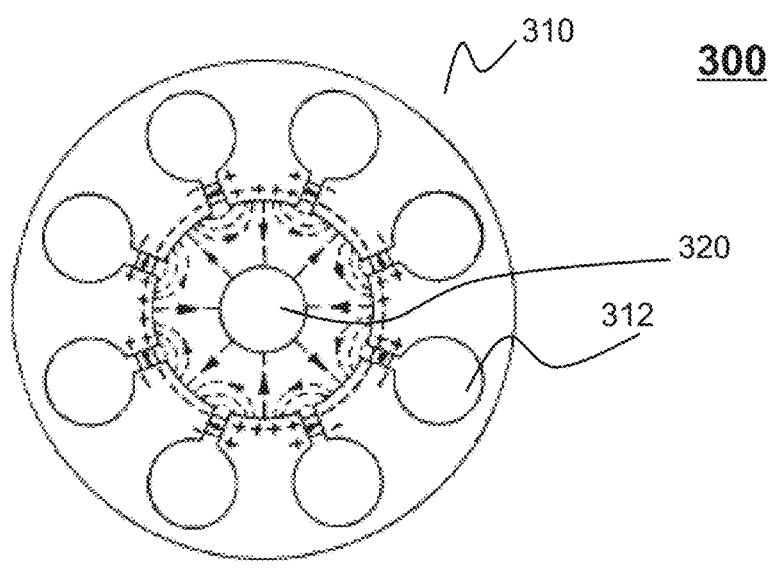
FIG. 3A illustrates a cross-sectional view of an exemplary microwave source according to some embodiments of the present disclosure.

FIG. 3A illustrates a cross-sectional view of an exemplary microwave source (e.g., a magnetron) according to some embodiments of the present disclosure. As shown in FIG. 3A, the microwave source 300 may include an anode block 310 and a cathode 320 centered in the anode block 310. The anode block 310 and the cathode 320 may be coaxial. In some embodiments, the anode block 310 may be fabricated into a cylindrical metal block (e.g., a copper block). The anode block 310 may include a plurality of resonant cavities 312. For different microwave sources, the number of the resonant cavities may be different. In some embodiments, the number of the resonant cavities may be from 8 to 20. Merely for illustration, the anode block 310 includes eight resonant cavities 312, that are, eight cylindrical holes around the cathode 320. An interaction space may be formed between the anode block 310 and the cathode 320, such as an open space between the anode block 310 and the cathode 320. In the interaction space, the electric and magnetic fields interact to exert force upon the electrons. The magnetic field is usually provided by a strong, permanent magnet mounted around the microwave source 300 so that the magnetic field is parallel with the axis of the cathode. The electrons released from the cathode 320 may travel outwardly in the interactive space. The released electrons can be accelerated toward to the anode block 310 by the action of pulsed DC electric field. The electrons may move in complex spirals towards the resonant cavities 312 due to the magnetic field. In some embodiments, the resonant cavities 312 may exist in various shapes, for example, include but not limited to a semicircular-shape cavity, a circular-shape cavity, a square-shape cavity, a rectangular-shape cavity, a fan-shape cavity, or the like, or any combination thereof.

Figure 3B:
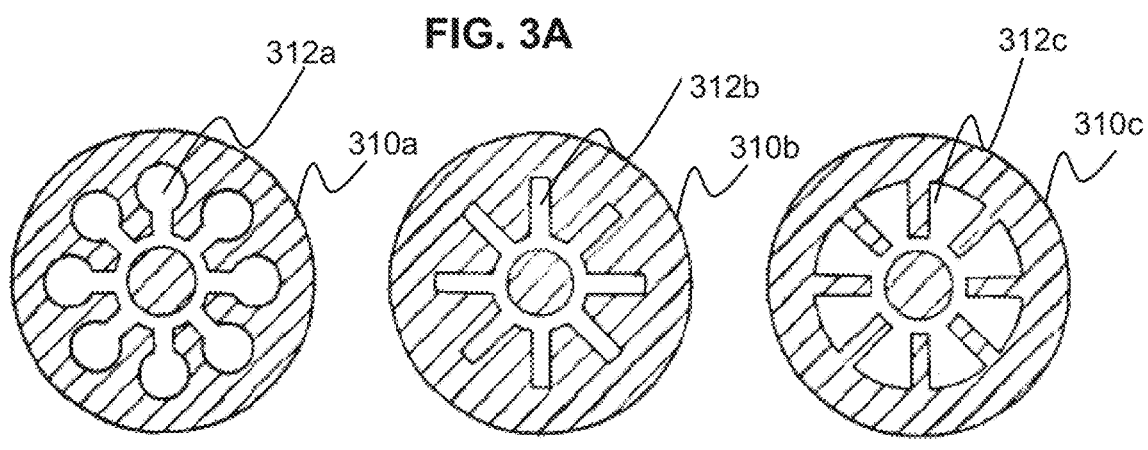
FIG. 3B illustrates different forms of an anode block in a microwave source according to some embodiments of the present disclosure.

FIG. 3B illustrates different forms of an anode block in a microwave source according to some embodiments of the present disclosure. As illustrated in FIG. 3B, anode block 310a may include a plurality of hole-and-slot type of resonant cavities 312a, anode block 310b may include a plurality of slot-type of resonant cavities 312b, and anode block 310c may include a plurality of vane-type of resonant cavities 312c. The resonant cavities may be usually arranged in a radial fashion.

Figure 3C:
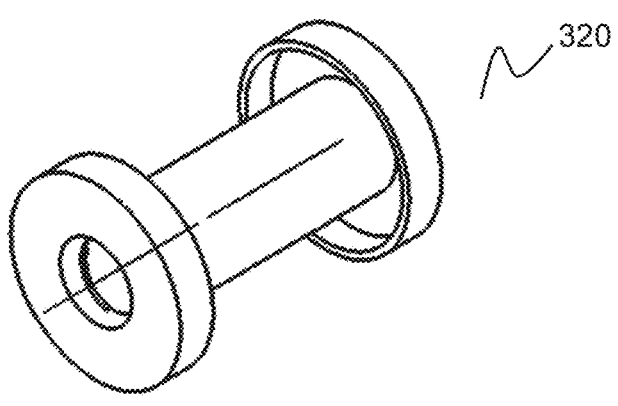
FIG. 3C illustrates an exemplary profile of a cathode of a microwave source according to some embodiments of the present disclosure.

FIG. 3C illustrates an exemplary profile of a cathode of a microwave source according to some embodiments of the present disclosure. As illustrated in FIG. 3C, the cathode 320 may include a hollow dumbbell-shape structure. In some embodiments, the cathode 320 may be made up of a hollow cylinder of emissive material (e.g., Barium Oxide) surrounding a cathode heater. For example, the cathode 320 may include a cathode heater and a thermionic emitter. The cathode heater may include at least one filament. The thermionic emitter may be made up of the hollow cylinder of emissive material. In some embodiments, the cathode heater may be fixed on a cathode support element (e.g., a cathode rod) in a spiral configuration. The cathode support element may be disposed in the hollow space of the thermionic emitter. When the cathode heater is heated by a power source, the outer thermionic emitter may release electrons due to a thermionic emission resulting from the heat radiation. Then the released electrons may travel outwardly in the direction of the anode block. As the electrons nip past the resonant cavities of the anode block, the energy may be passed to the resonant cavities, thus the resonant cavities may resonant at a certain resonant frequency and radiate energy in the form of microwaves.

Figure 4:
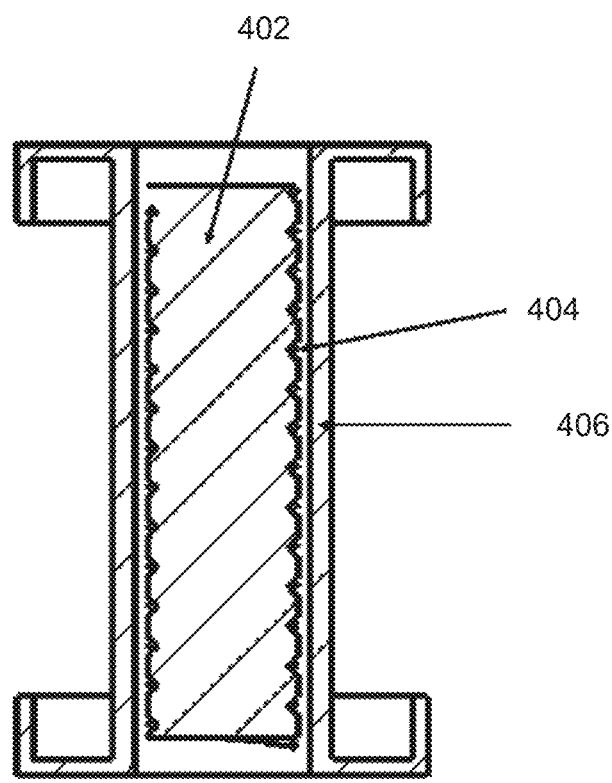
FIG. 4 illustrates a cross-sectional view of a cathode of a microwave source according to some embodiments of the present disclosure.

FIG. 4 illustrates a cross-sectional view of a cathode of a microwave source according to some embodiments of the present disclosure. As illustrated in FIG. 4, the cathode 320 may include a cathode support element 402, a cathode heater 404 and a thermionic emitter 406.

In some embodiments, a shape of the cathode support element 402 may be various, such as a cylinder, a cubic, a cone, and so on. The cross-sectional shape of the cathode support element 402 may be formed in a regular shape (e.g., a semicircle, a circle, a square, a triangle, a trapezoid, etc.) or an irregular shape (e.g., an irregular polygon). In some embodiments, the cathode support element 402 may be made of an insulative material. Exemplary insulative materials may include plastic, rubber, glass, ceramic, or the like, or any combination thereof. In some embodiments, the insulative cathode support element 402 may be formed as one body for reaching a high mechanical strength. The high-strength support element may facilitate to prolong the cathode's service life and guarantee its use reliability.

In some embodiments, the cathode support element 402 may include a plurality of slots for receiving the cathode heater 404. In some embodiments, the cathode heater 404 may be composed of at least one filament. The at least one filament may be placed in the plurality of slots when wounding around the cathode support element 404. In this way, each coiled segment (or each turn) of the at least one filament may be fixed due to the use of the slots. In some embodiments, the plurality of slots (e.g., slots 602a and 602b illustrated in FIG. 6) may be spaced axially around the circumference of the cathode support element 402. In some embodiments, each slot may accommodate a coiled segment when the at least one filament 402 wounds around the cathode support element 404. For example, a depth of the slot may be greater than or equal to a diameter of a filament, and a width of the slot may be greater than or equal to the dimeter of the filament. In some embodiments, the width of the slot may refer to a maximum width of the slot (e.g., the width of an opening of the slot).

In some embodiments, the filament may be made of a high-melting-point (e.g., >1000° C.) and conductive material. Exemplary filament materials may include tungsten, molybdenum, rhenium, iridium, or the like, or any combination thereof. In some embodiments, the diameter of the filament may be in the range of 0.2 mm to 2.0 mm. In some embodiments, the diameter of the filament may be in the range of 0.4 mm to 1.5 mm. In some embodiments, the diameter of the filament may be in the range of 0.4 mm to 0.8 mm. In some embodiments, the diameter of the filament may be 0.5 mm. It should be noted that any suitable filament diameter may be designed and not be limiting in the present disclosure.

Figures 5A, 5B:
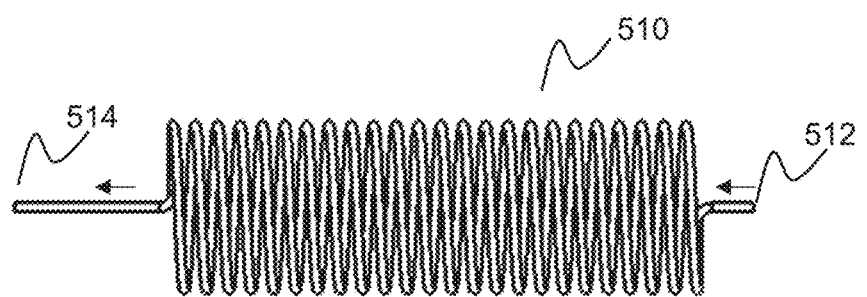
FIGS. 5A and 5B illustrates two exemplary forms of a filament arrangement according to some embodiments of the present disclosure.

FIGS. 5A and 5B illustrates two exemplary forms of a filament arrangement according to some embodiments of the present disclosure. As illustrated in FIG. 5A, filament 510 may be arranged into a single helix filament. Two leads of the filament 510 may be at the two ends of the filament 510. Coiled segments of the filament 510 extend in a one-way direction, for example, from a first lead 512 to a second lead 514. In some embodiments, when the filament 510 is powered on, a filament current in the filament 510 may be the one-way current (for any particular moment), for example, the current flows from the first lead 512 to the second lead 514. The direction of filament current in adjacent coiled segments (e.g., adjacent turns) are the same, which results in an interactive attractive force. Adjacent coiled segments may be shrunk due to the attractive force. When the filament 510 is powered off, the shrunk coiled segments are restored once the attractive force is disappeared. Since the filament 510 is frequently shrunk and restored, such deformation of the filament 510 may reduce the service life of the filament 510, and the service life of the cathode.

To resolve the aforementioned issue or similar issue that results in reduced service life, the cathode heater may include at least one filament in a double helix configuration. As illustrated in FIG. 5B, the filament 520 may be a double helix filament. In the structure of the double helix filament, two leads of the filament 520, such as a first lead 522 and a second lead 524, may be arranged at same side. In this case, the feeding wires electrically connected to the two leads can be led out from the same side. It is easy that the filament is mounted inside the microwave source lest that redundant feeding wires of the filament leads to a short circuit. A first part (e.g., first continuous coiled segments 523 connected to the first lead 522) of the filament 520 can spirally extend along a first direction parallel to a filament axis (e.g., axis 527 illustrated in a partial enlarged view 521) and in a first helix configuration. A second part (e.g., second continuous coiled segments 525 connected to the second lead 524) of the filament 520 can spirally extend along a second direction parallel to the filament axis and in a second helix configuration. The first direction and the second direction may be opposite and point to two ends of the filament axis. In some embodiments, the first part (e.g., the first continuous coiled segments 523) and the second part (e.g., the second continuous coiled segments 524) of the filament 520 may be operably connected in a loop form illustrated in 526. Coiled segments of the first part and the second part of the filament 520 may be interlaced and parallel substantially. In some embodiments, as illustrated in 521, when the filament 520 is powered on, directions of respective current flows of the first part and the second part of the filament 520 are inversed. Interactive force between the coiled segments may be counteracted due to the inversed currents. Compared with the single helix filament 510, the attractive force between adjacent coiled segments can be avoided, which may reduce the deformation of the filament. In some embodiments, the double helix filament may be composed of a single filament (or a single coil). In some embodiments, the double helix filament 520 may be composed of two filaments (or two coils). For example, the first part of the filament 520 may include a first filament and the second part of the filament 520 may include a second filament. A first end of the first filament can be designated as the first lead 522. A first end of the second filament can be designated of the second lead 524. A second end of the first filament can be electrically connected to a second end of the second filament in the loop form illustrated in 526.

Figure 6:
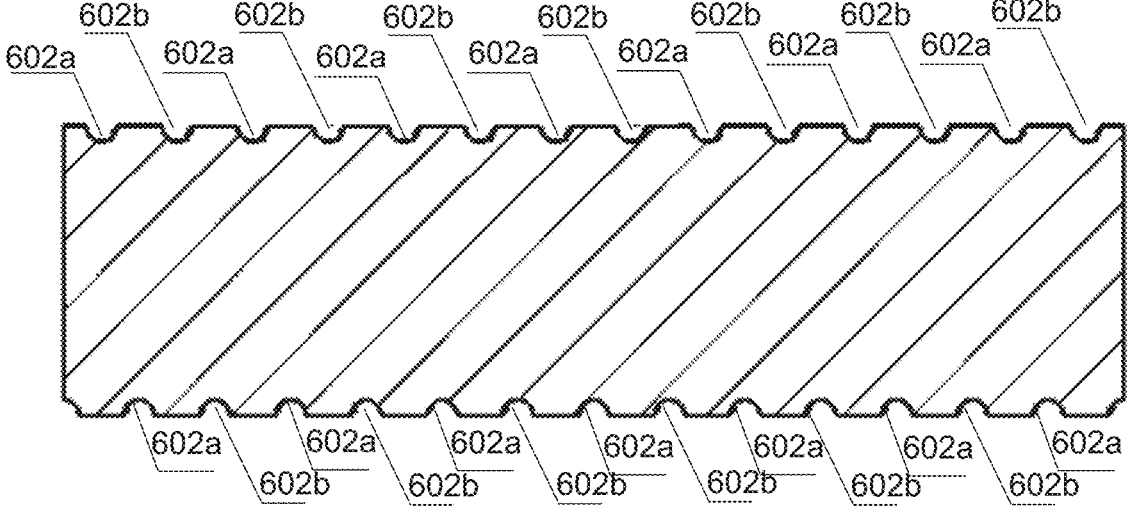
FIG. 6 illustrates a cross-sectional view of a cathode support element according to some embodiments of the present disclosure.

In some embodiments, to reduce the deformation of the filament (e.g., the filament 510 or 520), the filament can be spirally wound around a cathode support element having a plurality of slots. FIG. 6 illustrates a cross-sectional view of a cathode support element (e.g., the cathode support element 404 illustrated in FIG. 4) according to some embodiments of the present disclosure. As illustrated in FIG. 6, a plurality of slots (e.g., first slots 602a and second slots 602b) may be disposed on the cathode support element. The plurality of slots may be spaced axially around the circumference of the cathode support element. In some embodiments, a first portion of the plurality of slots (e.g., the first slots 602a) may be formed through a first continuous spiral groove radially around the circumference of the cathode support element. A second portion of the plurality of slots (e.g., the second slots 602b) may be formed through a second continuous spiral groove radially around the circumference of the cathode support element. The first slots 602a and the second slots 602b are interlaced axially. In some embodiments, a double helix filament (e.g., the filament 520 illustrated in FIG. 5B) may be placed in the plurality of slots so as to fix the filament and reduce the deformation of the filament. For example, the first part of the filament 520 may be received by the first slots 602*a* and the second part of the filament 520 may be received by the second slots 602*b*. In some embodiments, it is required that the size of a slot may be big enough to accommodate a coiled segment of the first part or the second part of the filament 520. For example, a depth of the slot (e.g., a slot 602*a* or 602*b*) may be greater than or equal to a diameter (e.g., 0.4 mm-0.8 mm) of the filament and a width of the slot may be greater than or equal to the dimeter of the filament.

Figure 7:
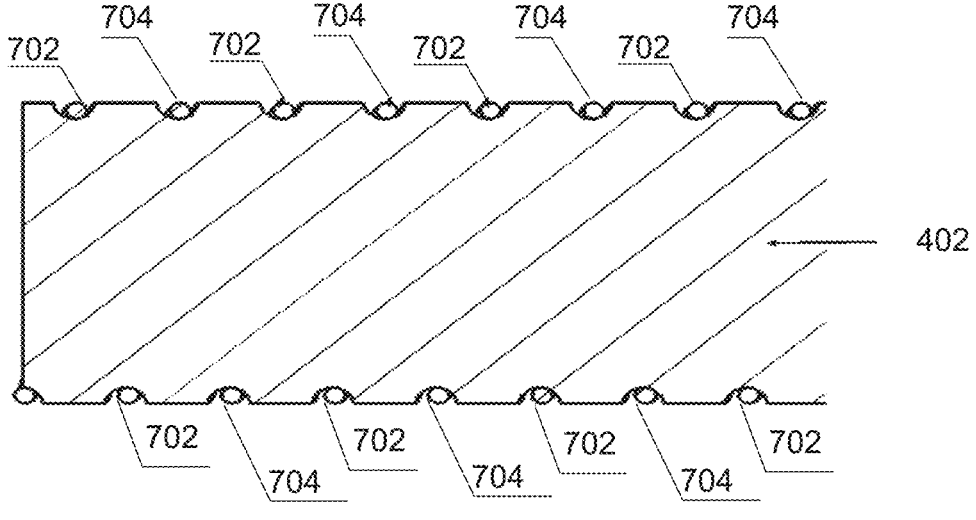
FIG. 7 illustrates a cross-sectional view of a filament wound around a cathode support element according to some embodiments of the present disclosure.

FIG. 7 illustrates a cross-sectional view of a filament wound around a cathode support element. For example, the double helix filament 520 is coiled around the cathode support element 402. The double helix filament 520 and the cathode support element 402 may be coaxial. Reference numeral 702 may represent a circular section of a coiled segment of the first part of the filament 520, and reference numeral 704 may represent a circular section of a coiled segmented of the second part of the filament 520.

Figure 8:
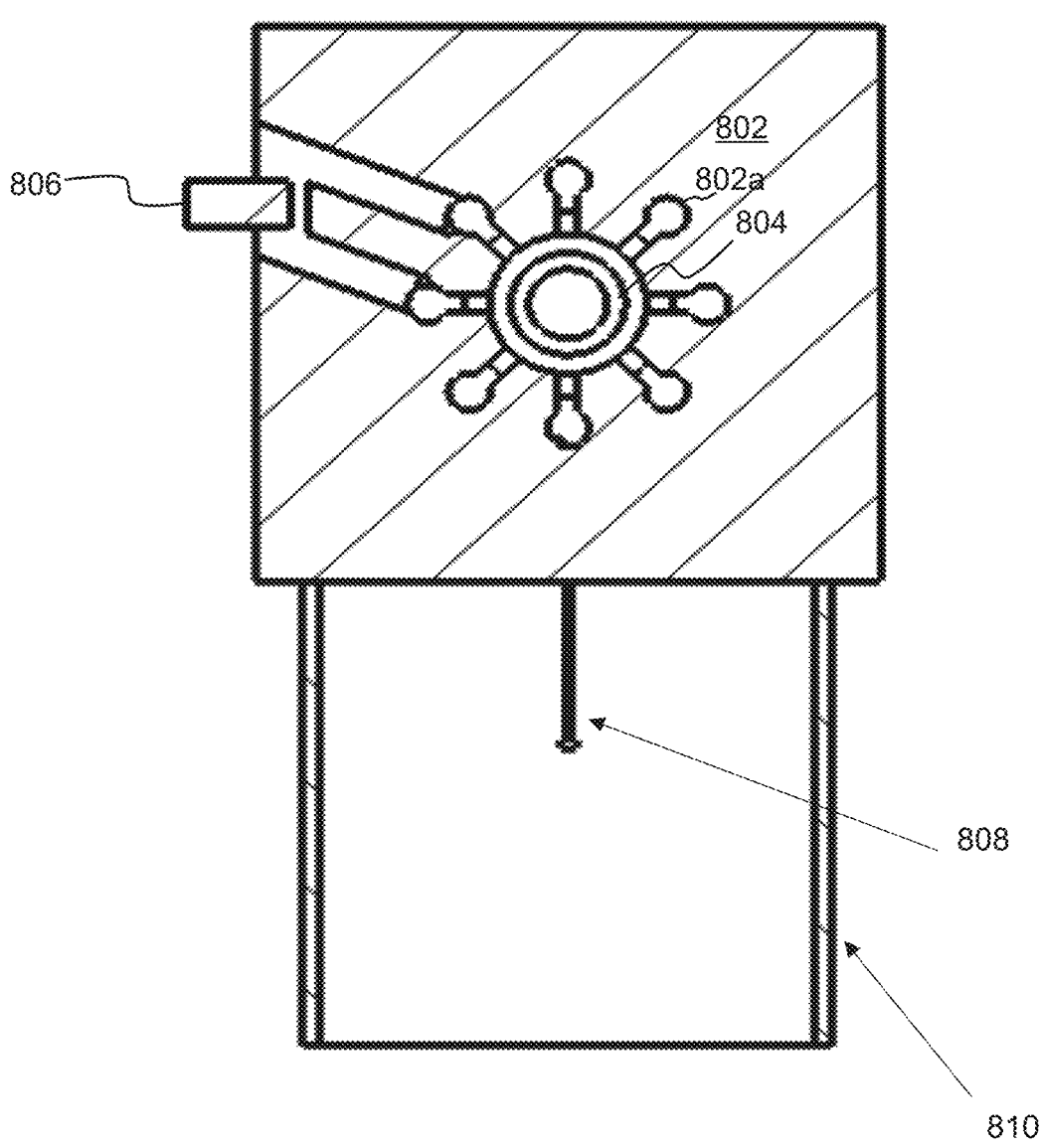
FIG. 8 illustrates a cross-sectional view of an exemplary microwave source according to some embodiments of the present disclosure.

FIG. 8 illustrates a cross-sectional view of an exemplary microwave source according to some embodiments of the present disclosure. Merely for illustration, microwave source 800 illustrated in FIG. 8 may be a magnetron. The magnetron may be a tunable magnetron. The microwave source 800 may include an anode block 802, a cathode 804 centered in the anode block 802, a tuning element 806, a microwave transmitter 808 and a transmission waveguide 810. As described in connection with FIGS. 3A and 3B, the anode block 802 may include a plurality of resonant cavities 802*a*. The resonant cavities 802*a* may exist in the form of the hole-and-slot type illustrated in FIG. 3B. The cathode 804 may be removably positioned in the center of the anode block. As described in connection with FIGS. 4-7, the cathode 804 may include a cathode heater, a thermionic emitter surrounding the cathode heater, and a cathode support element. The cathode heater may include a double helix filament. The double helix filament can spirally wound around the cathode support element and received by a plurality of slots on the cathode support element. More descriptions regarding the anode block and the cathode may be found elsewhere in the present disclosure (e.g., FIGS. 3A-7, and the descriptions thereof), and not repeated.

The tuning element 806 may be configured to adjust a resonant frequency of the microwave source 800. The resonant frequency may be changed by varying the inductance or capacitance of the resonant cavities of the microwave source. In some embodiments, the tuning element 806 may be inserted into the hole portion of the hole-and-slot cavities. The tuning element 806 may change the capacitance of the resonant cavities by altering the ratio of surface areas to cavity volume in a high-current region. The resonant frequency of the microwave source 800 may be adjusted higher or lower through an insertion or removal of the tuning element 806. For example, when the tuning element 806 is inserted into the anode hole, the capacitance of the cavity can be increased, thereby the resonant frequency may be decreased. In some embodiments, the microwave source 800 may include multiple tuning elements 806 operably connected to each resonant cavity 802*a*. Merely for illustrative purposes, just one tuning element 806 is illustrated. In some embodiments, the tuning element 806 may be made of an electrically conductive material (e.g., copper, aluminum, or other metal materials).

The microwave transmitter 808 may be configured to transmit the microwaves generated by the microwave source 800. The microwaves may be transmitted into the transmission waveguide 810 (e.g., the transmission waveguide illustrated in FIG. 2). Then transmission waveguide 810 may transmit the microwaves to an accelerator tube (e.g., the accelerator tube 210) in order to provide the kinetic energy to accelerate electrons in the accelerator tube.

Figure 9:
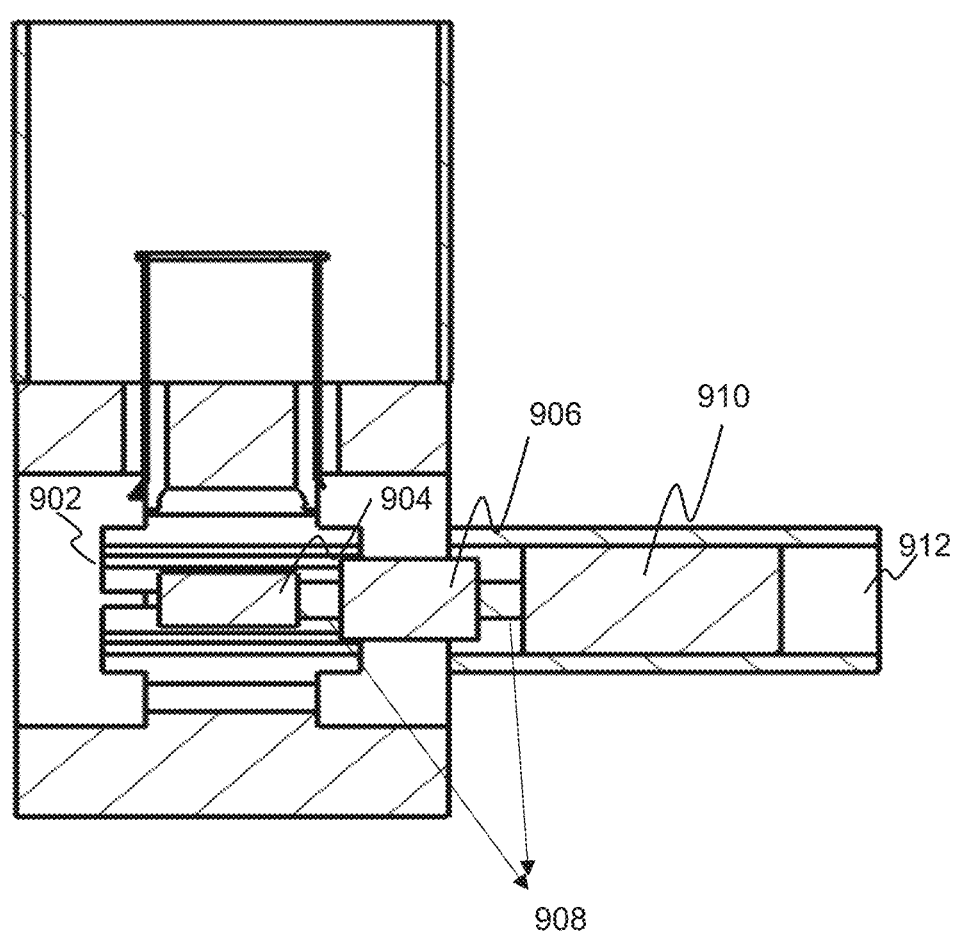
FIG. 9 illustrates a cross-sectional view of an exemplary microwave source according to some embodiments of the present disclosure.
Figure 10A:
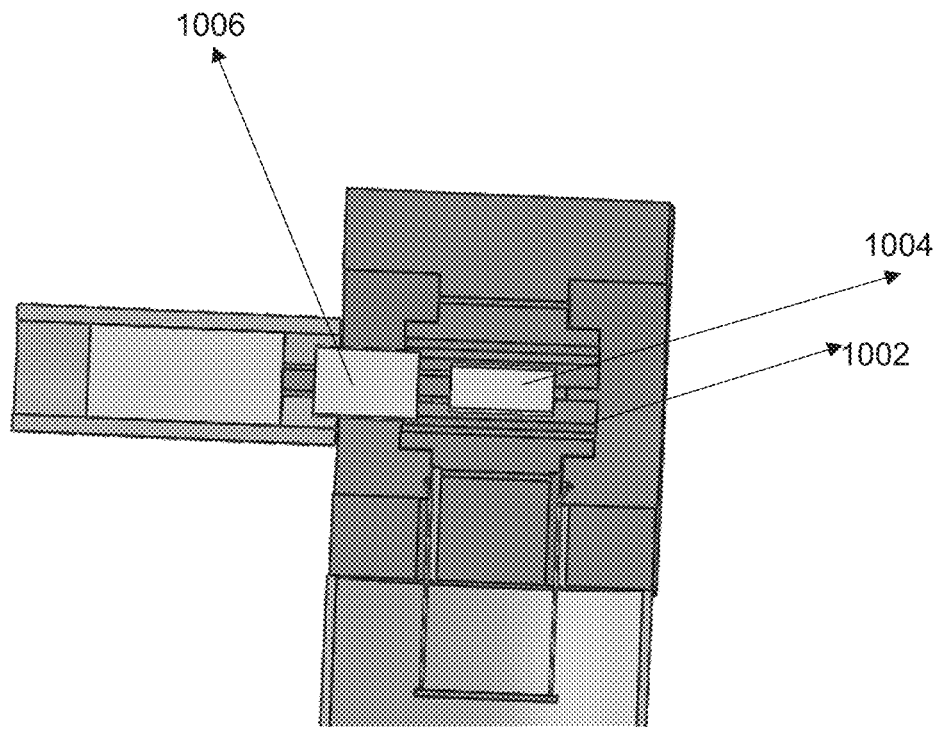
FIGS. 10A and 10B are schematic diagrams illustrating that different cathodes are positioned in a same anode block according to some embodiments of the present disclosure.
Figure 10B:
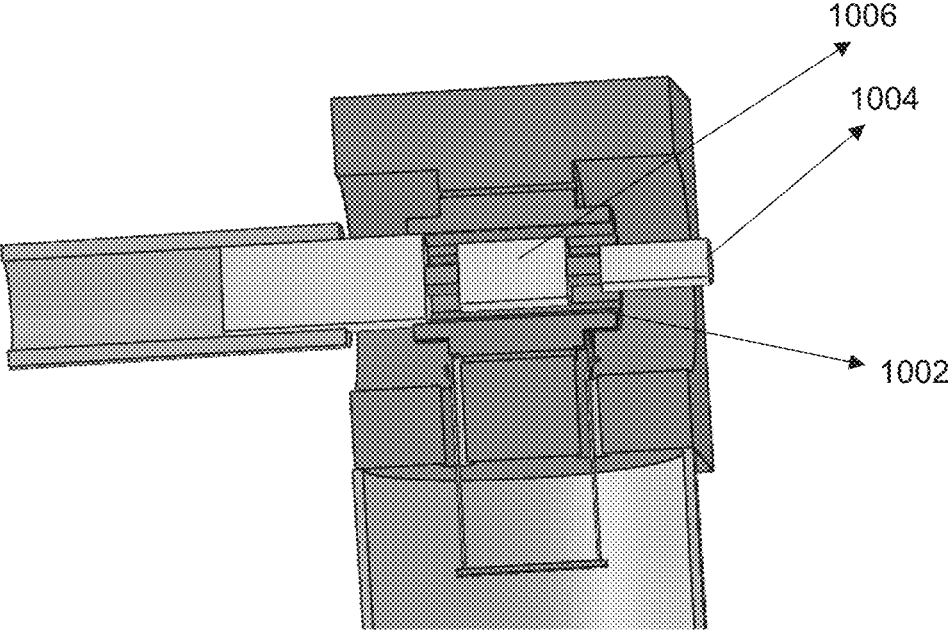

FIG. 9 illustrates a cross-sectional view of an exemplary microwave source according to some embodiments of the present disclosure. As illustrated in FIG. 9, microwave source 900 may be a multi-cathode microwave source (e.g., a multi-cathode magnetron). The microwave source 900 may include an anode block 902 and multiple cathodes, such as a first cathode 904 and a second cathode 906. In some embodiments, the multiple cathodes may be removably positioned in the center of the anode block 902. For example, as illustrated in FIG. 10A, a first cathode 1004 is positioned in the center of anode block 1002. As illustrated in FIG. 10B, second cathode 1006 is positioned in the center of anode block 1002. In some embodiments, when an individual cathode (e.g., the first cathode 904 or the second cathode 906) of the multiple cathodes is removably positioned in the center of the anode block, microwaves having a specific frequency (e.g., a specific microwave power) are generated in response to an occurrence of a resonance effect caused by the anode block and the cathode. More descriptions regarding the anode block and the cathode may be found elsewhere in the present disclosure (e.g., FIGS. 3A-7, and the descriptions thereof), and not be repeated.

In some embodiments, respective diameters of the multiple cathodes may be different. In some embodiments, the diameters of at least two of the multiple cathodes may be different. For example, the first cathode diameter may be 18 mm and the second cathode diameter may be 22 mm. In some embodiments, the microwave source 900 may include a connector 908. The multiple cathodes may be mechanically connected to each other by the connector 908. The connector 908 (e.g., a support rod) may be configured to support and connect each cathode. In some embodiments, the cathode support element (e.g., the cathode support element 402) may be a portion of the connector 908. The connector 908 may be made of an insulative material. In some embodiments, the microwave source 900 may include a limiting member 910. An end of the connector 908 may be operably connected to the limiting member 910. In some embodiments, the microwave source 900 may include a guide slot 912. The limiting member 910 may be disposed in the guide slot 912. In some embodiments, the limiting member 910 may move (e.g., slide) along the guide slot 912 in order to position the cathode of the multiple cathodes. For example, when the limiting member 910 is moved to a first location, the first cathode 904 can be positioned in the center of the anode block 902. When the limiting member 910 is moved to a second location, the second cathode 906 can be positioned in the center of the anode block 902 and the first anode cathode 904 may be moved out. In some embodiments, the limiting member 910 may be driven by various driving devices. Exemplary driving devices may include a hydraulic driver, a pneumatic driver, an electric actuator. In some embodiments, the various driving devices may not cause interferences for the generation of microwaves.

An electronic efficiency of the microwave source (e.g., the magnetron) may rely on a ratio of diameters of the cathode and the anode block (also referred to as "diameter ratio"). When the dimeter ratio is in a specific range, the electron efficiency may be at an optimal value, and an output power of the microwave source may be maximum. For example, for an eight-cavities anode block, when the diameter ratio is in the rage of 0.37-0.42, the electronic efficiency of the magnetron may be optimal. As another example, for a twelve-cavities anode block, when the diameter ratio is in the range of 0.50-0.58, the electronic efficiency of the magnetron may be optimal. As a further example, for a sixteen-cavities anode block, when the diameter ratio is in the range of 0.60-0.66, the electronic efficiency of the magnetron may be optimal.

In some embodiments, the output power of the microwave source can be changed by varying the diameter ratio of the anode block to the cathode. In some embodiments, for a specific anode block, the diameter ratio can be changed by alternating the cathodes having different diameters. Merely for illustration, for a magnetron including a twelve-cavities anode block, its resonant frequency is 2998 MHz and maximum output power is 3.4 MW. Given that the diameter of the anode block is 34 mm. The maximum output power of the magnetron can be reached only if the diameter of the cathode in the range of 17-19.72 mm. It is understood that, when the diameter of a cathode is less than 17 mm or greater than 19.72 mm, the magnetron may output a relatively small microwave power. By arranging the constant anode block and one of the cathodes having different diameters, the magnetron may output alternative microwave powers. The alternative microwave powers may be used to generate radiation beams of different energies. For example, the diameter of the anode block 902 is set as 34 mm and the diameter of the first cathode 904 is set as 18 mm. When the anode block 902 and the first cathode 904 are powered on, the microwave source 900 may output the maximum microwave power for accelerating electrons in the accelerator tube 210 to generate therapeutic radiation beams. The therapeutic radiation beams may be applied to the target object for eliminating tumor tissues. As another example, the diameter of the second cathode 906 is set as 22 mm. When the anode block 902 and the second cathode 906 are powered on, the microwave source 900 may output a relatively small microwave power for accelerating electrons in the accelerator tube 210 to generate imaging radiation beams. For the IGRT device, the imaging radiation beams may be used to image a region of interest (ROI) related to the target object. The radiotherapy procedure may be guided according to the ROI related information (e.g., a tumor region).

In some embodiments, the resonant frequency of the microwave source can be changed by alternating different cathodes. The resonant frequency of the microwave source may rely on an equivalent capacitance and inductance of the microwave source. For example, the resonant frequency, $f=1/\sqrt{LC}$ where L denotes the inductance and C denotes the equivalent capacitance. For the constant anode block, the larger the diameter of the cathode, the smaller the distance between the cathode and the anode block, thereby the equivalent capacitance becomes larger. The resonant frequency may be changed with the equivalent capacitance. In some embodiments, by switching cathodes of different diameters, different resonant frequency may be produced accordingly. In addition, the tuning element (e.g., the tuning element 806) of the microwave source may slightly adjust the resonant frequency, such as ±5 MHz. The adjustable range of the resonant frequency of the microwave source may be enlarged due to the use of the multiple cathodes and the tuning element. It is understood that the frequencies of output microwaves may be changed varying with the characteristics (e.g., resonant frequencies) of the microwave source. Specific microwave frequency may be produced when different cathodes are applied.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A microwave source, comprising:
an anode block; and
multiple cathodes,
wherein when an individual cathode of the multiple cathodes is removably positioned in a center of the anode block, microwaves having a specific frequency are generated in response to an occurrence of a resonance effect caused by the anode block and the cathode.

2. The microwave source of claim 1, wherein diameters of at least two of the multiple cathodes are different.

3. The microwave source of claim 1, wherein each of the multiple cathodes includes:
a cathode support element having a plurality of slots, the plurality of slots being axially around a circumference of the cathode support element; and
a cathode heater including at least one filament,
wherein a first part of the at least one filament is wound around the cathode support element along a first direction and received by a first portion of the plurality of slots, and a second part of the at least one filament is wound around the cathode support element along a second direction and received by a second portion of the plurality of slots.

4. The microwave source of claim 3, wherein the first part of the at least one filament and the second part of the at least one filament are substantially parallel, and when the at least one filament is powered by a power source, directions of respective current flows of the first part and the second part of the at least one filament are inversed.

5. The microwave source of claim 3, wherein the first portion of the plurality of slots and the second portion of the plurality of slots are spaced axially around the circumference of the cathode support element.

6. The microwave source of claim 5, wherein the diameter of the filament is in a range of 0.4 mm to 0.8 mm.

7. The microwave source of claim 3, wherein a depth of a slot of the plurality of slots is greater than or equal to a diameter of one of the at least one filament, and a width of the slot is greater than or equal to the diameter of the filament.

8. The microwave source of claim 3, wherein the at least one filament is made of a high-melting-point and conductive material.

9. The microwave source of claim 8, wherein the at least one filament includes at least one of tungsten, molybdenum, rhenium, or iridium.

10. The microwave source of claim 3, wherein the cathode support element is made of an insulative material.

11. The microwave source of claim 3, further comprising:
a thermionic emitter configured to release electrons when the thermionic emitter is heated by the cathode heater.

12. The microwave source of claim 3, wherein the first part of the at least one filament is electrically connected to the second part of the at least one filament.

13. The microwave source of claim 3, wherein a value of a current flow of the first part is the same as a value of a current flow of the second part.

14. The microwave source of claim 3, wherein the plurality of slots are formed through a continuous spiral groove radially around the circumference of the cathode support element.

15. The microwave source of claim 1, further comprising: a connector configured to connect each of the multiple cathodes.

16. The microwave source of claim 15, further comprising: a limiting member connected to an end of the connector and configured to move the multiple cathodes.

17. The microwave source of claim 16, wherein the limiting member is moved along a guiding slot such that one of the multiple cathodes is positioned in the center of the anode block.

18. A radiotherapy device including a linear accelerator, the linear accelerator comprising:

an electron generator configured to emit electrons along a beam path;

the microwave source according to claim 14; and an accelerator tube configured to accelerate the electrons emitted by the electron generator in response to the microwaves having the specific frequency.

19. A cathode, comprising:

a cathode support element having a slot, the slot being axially around a circumference of the cathode support element;

a cathode heater, and a thermionic emitter, wherein the thermionic emitter includes a hollow cylinder of emissive material, and the cathode support element is disposed in a hollow space of the thermionic emitter.

20. The cathode of claim 19, wherein the cathode heater is fixed on the cathode support element in a spiral configuration.

\*    \*    \*    \*    \*